(12) United States Patent
Nicolaides et al.

(10) Patent No.: US 7,829,338 B2
(45) Date of Patent: *Nov. 9, 2010

(54) METHOD FOR GENERATING HYPERMUTABLE ORGANISMS

(75) Inventors: Nicholas Nicolaides, Boothwyn, PA (US); Bert Vogelstein, Baltimore, MD (US); Kenneth Kinzler, BelAir, MD (US)

(73) Assignee: The Johns Hopkins University, Baltimore, MD (US)

( * ) Notice: Subject to any disclaimer, the term of this patent is extended or adjusted under 35 U.S.C. 154(b) by 81 days.

This patent is subject to a terminal disclaimer.

(21) Appl. No.: 11/907,338

(22) Filed: Oct. 11, 2007

(65) Prior Publication Data

US 2008/0313754 A1 Dec. 18, 2008

Related U.S. Application Data

(60) Continuation of application No. 09/558,149, filed on Apr. 26, 2000, now Pat. No. 7,297,837, which is a division of application No. 09/059,461, filed on Apr. 14, 1998, now Pat. No. 6,146,894.

(51) Int. Cl.
C12N 15/00 (2006.01)
C12N 5/00 (2006.01)
C12N 5/02 (2006.01)
C12N 15/74 (2006.01)
C12Q 1/68 (2006.01)

(52) U.S. Cl. .................... 435/440; 435/455; 435/325; 435/6; 435/471

(58) Field of Classification Search .................. 435/440
See application file for complete search history.

(56) References Cited

U.S. PATENT DOCUMENTS

| 5,907,079 | A | 5/1999 | Mak et al. |
| 6,146,894 | A | 11/2000 | Nicolaides et al. |
| 6,191,268 | B1 | 2/2001 | Liskay et al. |
| 6,287,862 | B1 | 9/2001 | delCardayre et al. |

FOREIGN PATENT DOCUMENTS

| WO | WO 97/08312 | 3/1997 |
| WO | WO 99/19492 | 4/1999 |

OTHER PUBLICATIONS

Prolla, 1998, Current Opinions in Cell Biology, 10:311-316.*
Baarends, 2001, Reproduction, 121:31-39.*
Allen, D., et al., "MutS mediates heteroduplex loop formation by a translocation mechanism" *EMBO J.*, 1997, 16(14), 4467-4476.
Baker, S.M., et al., "Male mice defective in the DNA mismatch repair gene PMS2 exhibit abnormal chromosome synapsis in meiosis" *Cell*, 1995, 82, 309-319.
Bronner C.E., et al., "Mutation in the DNA mismatch repair gene homologue hMLH1 is associated with hereditary non-polyposis colon cancer" *Nature*, 1994, 368, 258-261.
de Wind, N., et al., "Inactivation of the mouse Msh2 gene results in mismatch repair deficiency, methylation tolerance, hyperrecombination, and predisposition to cancer" *Cell*, 1995, 82, 321-330.
Drummond, J.T., et al., "Isolation of an hMSH2-p160 heterodimer that restores DNA mismatch repair to tumor cells" *Science*, 1995, 268, 1909-1912.
Drummond, J.T., et al., "Cisplatin and adriamycin resistance are associated with mutlα and mismatch repair deficiency in an ovarian tumor cell line" *J. Biological Chemistry*, 1996, 271(33), 19645-19648.
Edelmann, W., et al., "Meiotic pachytene arrest in MLH1-deficient mice" *Cell*, 1996, 85, 1125-1134.
Eshleman, J.R., et al., "Mismatch repair defects in human carcinogenesis" *Human Molecular Genetics*, 1996, 5, 1489-1494.
Fishel, R. et al., "The human mutator gene homolog MSH2 and its association with hereditary nonpolyposis colon cancer." *Cell* 1993, 7:1027-1038.
Galio, L., et al., "ATP hydrolysis-dependent formation of a dynamic ternary nucleoprotein complex with MutS and MutL" *Nucleic Acids Research*, 1999, 27(11), 2325-2331.
Hamilton, S.R. et al. "The molecular basis of Turcot's syndrome." *N. Eng. J. Med.* 1995, 332:839-847.
Harfe, B.D., "DNA mismatch repair and genetic instability" *Annu. Rev. Genet.*, 2000, 34, 359-399.
Hoang J., et al., "BAT-26, an Indicator of the Replication Error Phenotype in Colorectal Cancers and Cell Lines" *Cancer Res.*, 1997, 57, 300-303.
Holmes, J., S. Clark, and P. Modrich, "Strand-specific mismatch correction in nuclear extracts of human and *Drosophila melanogaster* cell lines" *Proc. Natl. Acad. Sci. USA* 1990 87:5837-5841.
Honma, M. et al., "Cytotoxic and Mutagenic Responses to X-rays and Chemical Mutagens in Normal and p53-mutated Human Lymphoblastoid Cells" *Mut. Res.*, 1997, 374, 89-98.
Jiricny, J., et al., "Mismatch repair defects in cancer" *Curr. Opin. Genet. Dev.*, 2000, 10, 157-161.
Karran, P., et al., "Genomic instability and tolerance to alkylating agents" *Cancer Surveys*, 1996, 28, 69-71.
Leach, F.S., et al., "Mutations of a mutS homolog in hereditary nonpolyposis colorectal cancer" *Cell*, 1993, 75, 1215-1225.
Li, G.-M. and P. Modrich. "Restoration of mismatch repair to nuclear extracts of H6 colorectal tumor cells by a heterodimer of human MutL homologs" *Proc. Natl. Acad. Sci. USA* 1995 92:1950-1954.
Liu, T., et al., "Microsatellite instability as a predictor of a mutation in a DNA mismatch repair gene in familial colorectal cancer" *Genes, Chromosomes & Cancer*, 2000, 27, 17-25.
Liu, T., et al., "Microsatellite instability as a predictor of a mutation in a DNA mismatch repair gene in familial colorectal cancer" *Genes. Chromosomes & Cancer*, 2000, 27, 17-25.

(Continued)

*Primary Examiner*—Valarie Bertoglio
(74) *Attorney, Agent, or Firm*—Banner & Witcoff, Ltd.

(57) ABSTRACT

Dominant negative alleles of human mismatch repair genes can be used to generate hypermutable cells and organisms. By introducing these genes into cells and transgenic animals, new cell lines and animal varieties with novel and useful properties can be prepared more efficiently than by relying on the natural rate of mutation.

2 Claims, 6 Drawing Sheets

OTHER PUBLICATIONS

Liu et al., "Analysis of Mismatch Repair Genes in Hereditary Non-polyposis Colorectal Cancer Patients" *Nature Medicine*, Feb. 1996, 2(2), 169-174.

Ma et al., "Dominant Negative Expression of hPMS2 Creates Isogenic Mismatch Repair Deficient Human Colon Cancer Cell Lines" *Proc. Am. Assoc. Cancer Res.*, Mar. 1998, 39, p. 460 (Abstract #3130).

McCallum, C.M., "Targeted screening for induced mutations" *Nature Biotechnology*, 2000, 18, 455-457.

Modrich, P., "Mismatch repair, genetic stability, and cancer" *Science*, 1994, 266, 1959-1960.

Nicolaides, et al., "The jun family members, c-jun and junD, transactivate the human c-*myb*, promotor via an Ap1-like element" *J. Biological Chemistry*, 1992, 267(27), 19655-19672.

Nicolaides et al., "Genomic organization of the human *PMS2* gene family" *Genomics*, 1995, 30, 195-206.

Nicolaides et al. "Molecular cloning of the N- terminus of GTBP." *Genomics* 1996, 31:395-397.

Nicolaides et al., "Positive autoregulation of c-*myb*, expression via Myb binding sites in the 5' flanking region of the human c-*myb* gene" *Molecular and Cellular Biology*, 1991, 11(12), 6166-6176.

Nicolaides et al., "Analysis of the 5' region of *PMS2* reveals heterogeneous transcripts and a novel overlapping gene" *Genomics*, 1995, 29, 329-334.

Palombo, F., et al., "Mismatch repair and cancer" *Nature*, 1994, 367, 417.

Pang, Q., T.A. Prolla and R.M. Liskay, "Functional domains of the *Saccharomyces cerevisiae* Mlh1p and Pms1p DNA mismatch repair proteins and their relevance to human hereditary nonpolyposis colorectal cancer-associated mutations" *Mol. Cell. Biol.* 1997 17(8):4465-4473.

Papadopoulos, N., et al., "Mutation of a *mutL* homolog in hereditary colon cancer" *Science*, 1994, 263, 1625-1629.

Papadopoulos, N., et al., "Mutations of *GTBP* in genetically unstable cells" *Science*, 1995, 268, 1915-1917.

Parsons, R. et al. "Mismatch repair deficiency in phenotypically normal human cells." *Science* 1995 268:738-740.

Parsons, R., et al., "hypermutability and mismatch repair deficiency in RER+ tumor cells" *Cell*, 1993, 75, 1227-1236.

Peinado, M.A., et al., "Isolation and characterization of allelic losses and gains in colorectal tumors by arbitrarily primed polymerase chain reaction" *Proc. Natl. Acad. Sci. USA*, 1992, 89, 10065-10069.

Perucho, M., et al., "Cancer of the microsatellite mutator phenotype" *Biol. Chem.*, 1996, 377, 675-684.

Prolla, T.A., et al., "MLH1, PMS1, and MSH2 interactions during the initiation of DNA mismatch repair in yeast" *Science*, 1994, 265, 1091-1093.

Quian, Y. et al., "Molecular events after antisense inhibition of hMSH2 in a HeLa cell line" *Mutation Research*, Oct. 12, 1998, vol. 418, pp. 61-71.

Spampinato, C., et al., "The MutL ATPase is required for mismatch repair" *J. Biological Chemistry*, 2000, 275(13), 9863-9869.

Strand, M., et al., "Destabilization of tracts of simple repetitive DNA in yeast by mutations affecting DNA mismatch repair" *Nature*, 1993, 365, 274-276.

Su, S., et al., "Mispair specificity of methyl-directed DNA mismatch correction in vitro" *J. Biological Chemistry*, 1988, 263(14), 6829-6835.

Vora, K.A. et al., "Severe Attenuation of the B Cell Immune Response in Msh2-deficient Mice" *Journal of Experimental Medicine*, Feb. 1999, 189(3), 471-481.

Wheeler, J.M.D., et al., "The role of hypermethylation of the *hMLH*1 promoter region in HNPCC verus MSI+sporadic colorectal cancers" *J. Med. Genet.*, 2000, 588-592.

Winter, D.B. et al., "Altered spectra of hypermutation in antibodies from mice deficient for the DNA mismatch repair protein PMS2" *Proc. Natl. Acad. Sci., USA*, Jun. 1998, 95, 6953-6958.

Glabb et al., Carcinogenesis 18:1-8, 1997.

Nicolaides et al., Nature 371:75-80, 1994.

C. Bonnerot et al., "Transcriptional Selectivity in Early Mouse Embryos: A Qualitative Study," Nucl Acids Res, 1991, 19:7251-7257.

Overbeek, "Factors Affecting Transgenic Animal Production," Transgenic Animal Technology, 1994, pp. 96-98.

Kappell, Current Opinions in Biotechnology, 1992, vol. 3, pp. 548-553.

CD Sigmund, "Viewpoint: Are Studies in Genetically Altered Mice Out of Control," Arterioscler Thromb Vasc Bio., Jun. 2000, 20:1425-1429.

JJ Mullins et al., "Transgenesis in Nonmurine Species," Hypertension, Oct. 1993, vol. 22, No. 4, pp. 630-633.

GE Seidel, Jr., "Resource Requirements for Transgenic Livestock Research," J. Anim. Sci., 1993, 71(Suppl.3):26-33.

Re Hammer et al., "Spontaneous Inflammatory Disease in Transgenic Rats Expressing HLA-B27 and Human Beta2m: An Animal Model of HLA-B27-Associated Human Disorders," Cell, Nov. 1990, vol. 63, pp. 1099-1112.

ER Cameron, "Recent Advances in Transgenic Technology," Molecular Biotechnology, 1997, vol. 7, pp. 253-265.

Wall, "Transgenic Livestock: Progress and Prospects for the Future," Theriogenology, 1996, vol. 45, pp. 57-68.

Definition of "allele" http://216.251.232I59/semdweb/internetsomd/ASP/14877.14.asp, printout attached.

Nicolaides et al., Mol. Cell. Biol., 1998, 18:1635-1641.

\* cited by examiner

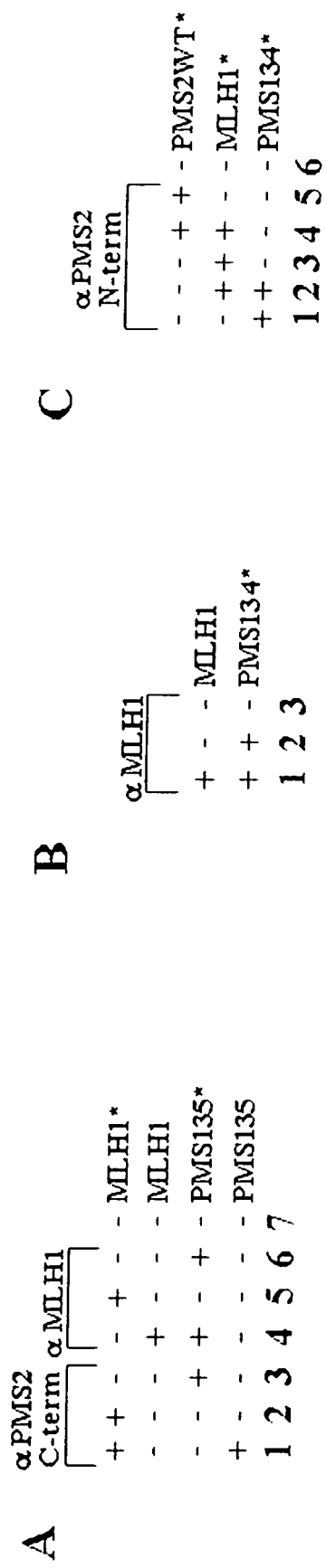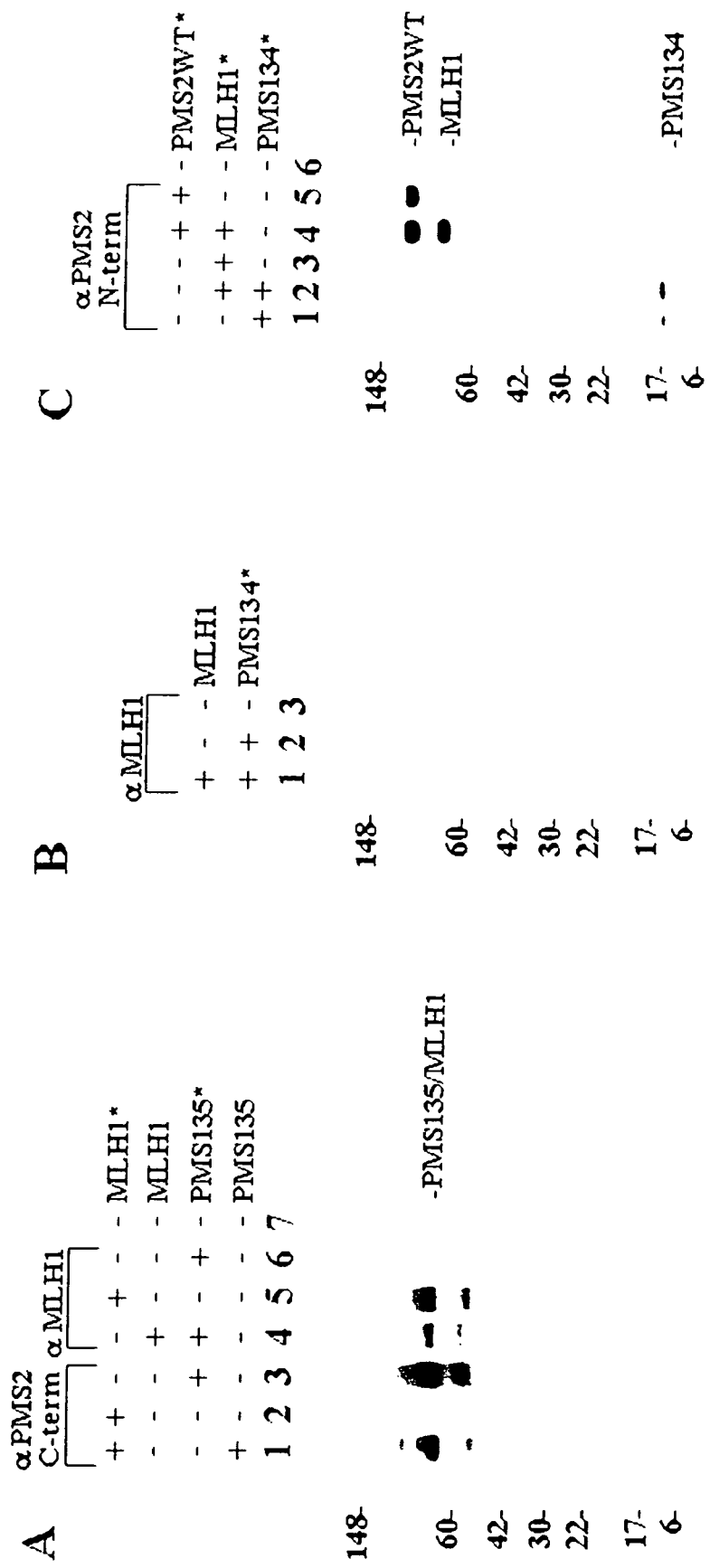

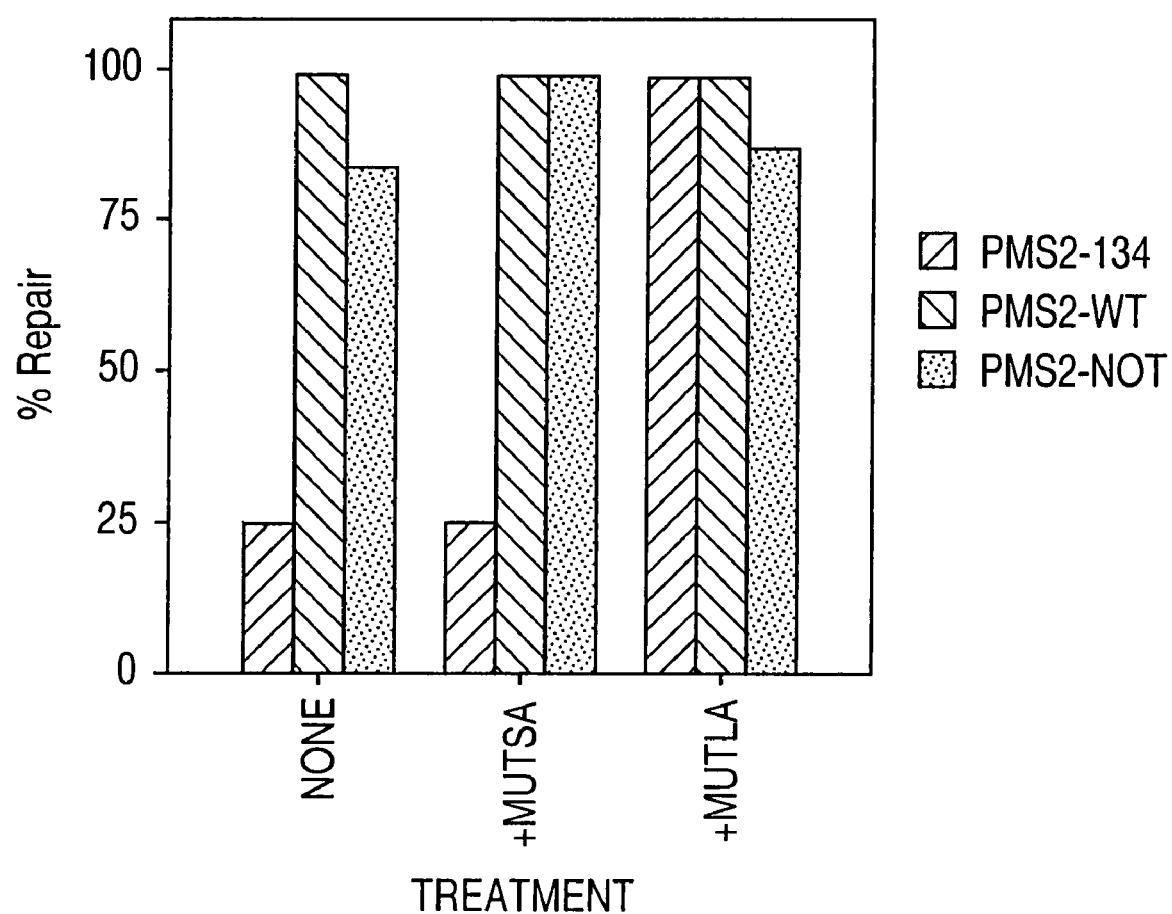

SEQUENCE LISTING

<160> NUMBER OF SEQ ID NOS: 8

<210> SEQ ID NO 1
<211> LENGTH: 2771
<212> TYPE: DNA
<213> ORGANISM: Homo sapiens
<220> FEATURE:
<221> NAME/KEY: CDS
<222> LOCATION: (25)...(2610)

<400> SEQUENCE: 1

```
cgaggcggat cgggtgttgc atcc atg gag cga gct gag agc tcg agt aca           51
                          Met Glu Arg Ala Glu Ser Ser Ser Thr
                           1               5 gaa cct gct aag gcc atc aaa cct att gat cgg aag tca gtc cat cag          99
Glu Pro Ala Lys Ala Ile Lys Pro Ile Asp Arg Lys Ser Val His Gln
 10                  15                  20                  25 att tgc tct ggg cag gtg gta ctg agt cta agc act gcg gta aag gag         147
Ile Cys Ser Gly Gln Val Val Leu Ser Leu Ser Thr Ala Val Lys Glu
                 30                  35                  40 tta gta gaa aac agt ctg gat gct ggt gcc act aat att gat cta aag         195
Leu Val Glu Asn Ser Leu Asp Ala Gly Ala Thr Asn Ile Asp Leu Lys
             45                  50                  55 ctt aag gac tat gga gtg gat ctt att gaa gtt tca gac aat gga tgt         243
Leu Lys Asp Tyr Gly Val Asp Leu Ile Glu Val Ser Asp Asn Gly Cys
         60                  65                  70 ggg gta gaa gaa gaa aac ttc gaa ggc tta act ctg aaa cat cac aca         291
Gly Val Glu Glu Glu Asn Phe Glu Gly Leu Thr Leu Lys His His Thr
     75                  80                  85 tct aag att caa gag ttt gcc gac cta act cag gtt gaa act ttt ggc         339
Ser Lys Ile Gln Glu Phe Ala Asp Leu Thr Gln Val Glu Thr Phe Gly
 90                  95                 100                 105 ttt cgg ggg gaa gct ctg agc tca ctt tgt gca ctg agc gat gtc acc         387
Phe Arg Gly Glu Ala Leu Ser Ser Leu Cys Ala Leu Ser Asp Val Thr
                110                 115                 120 att tct acc tgc cac gca tcg gcg aag gtt gga act cga ctg atg ttt         435
Ile Ser Thr Cys His Ala Ser Ala Lys Val Gly Thr Arg Leu Met Phe
            125                 130                 135 gat cac aat ggg aaa att atc cag aaa acc ccc tac ccc cgc ccc aga         483
Asp His Asn Gly Lys Ile Ile Gln Lys Thr Pro Tyr Pro Arg Pro Arg
        140                 145                 150 ggg acc aca gtc agc gtg cag cag tta ttt tcc aca cta cct gtg cgc         531
Gly Thr Thr Val Ser Val Gln Gln Leu Phe Ser Thr Leu Pro Val Arg
    155                 160                 165 cat aag gaa ttt caa agg aat att aag aag gag tat gcc aaa atg gtc         579
His Lys Glu Phe Gln Arg Asn Ile Lys Lys Glu Tyr Ala Lys Met Val
170                 175                 180                 185 cag gtc tta cat gca tac tgt atc att tca gca ggc atc cgt gta agt         627
Gln Val Leu His Ala Tyr Cys Ile Ile Ser Ala Gly Ile Arg Val Ser
                190                 195                 200 tgc acc aat cag ctt gga caa gga aaa cga cag cct gta gta tgc aca         675
Cys Thr Asn Gln Leu Gly Gln Gly Lys Arg Gln Pro Val Val Cys Thr
            205                 210                 215 ggt gga agc ccc agc ata aag gaa aat atc ggc tct gtg ttt ggg cag         723
Gly Gly Ser Pro Ser Ile Lys Glu Asn Ile Gly Ser Val Phe Gly Gln
        220                 225                 230 aag cag ttg caa agc ctc att cct ttt gtt cag ctg ccc cct agt gac         771
Lys Gln Leu Gln Ser Leu Ile Pro Phe Val Gln Leu Pro Pro Ser Asp
    235                 240                 245
```

```
tcc gtg tgt gaa gag tac ggt ttg agc tgt tcg gat gct ctg cat aat    819
Ser Val Cys Glu Glu Tyr Gly Leu Ser Cys Ser Asp Ala Leu His Asn
250             255                 260                 265 ctt ttt tac atc tca ggt ttc att tca caa tgc acg cat gga gtt gga    867
Leu Phe Tyr Ile Ser Gly Phe Ile Ser Gln Cys Thr His Gly Val Gly
                270                 275                 280 agg agt tca aca gac aga cag ttt ttc ttt atc aac cgg cgg cct tgt    915
Arg Ser Ser Thr Asp Arg Gln Phe Phe Phe Ile Asn Arg Arg Pro Cys
            285                 290                 295 gac cca gca aag gtc tgc aga ctc gtg aat gag gtc tac cac atg tat    963
Asp Pro Ala Lys Val Cys Arg Leu Val Asn Glu Val Tyr His Met Tyr
300                 305                 310 aat cga cac cag tat cca ttt gtt gtt ctt aac att tct gtt gat tca   1011
Asn Arg His Gln Tyr Pro Phe Val Val Leu Asn Ile Ser Val Asp Ser
    315                 320                 325 gaa tgc gtt gat atc aat gtt act cca gat aaa agg caa att ttg cta   1059
Glu Cys Val Asp Ile Asn Val Thr Pro Asp Lys Arg Gln Ile Leu Leu
330                 335                 340                 345 caa gag gaa aag ctt ttg ttg gca gtt tta aag acc tct ttg ata gga   1107
Gln Glu Glu Lys Leu Leu Leu Ala Val Leu Lys Thr Ser Leu Ile Gly
            350                 355                 360 atg ttt gat agt gat gtc aac aag cta aat gtc agt cag cag cca ctg   1155
Met Phe Asp Ser Asp Val Asn Lys Leu Asn Val Ser Gln Gln Pro Leu
        365                 370                 375 ctg gat gtt gaa ggt aac tta ata aaa atg cat gca gcg gat ttg gaa   1203
Leu Asp Val Glu Gly Asn Leu Ile Lys Met His Ala Ala Asp Leu Glu
        380                 385                 390 aag ccc atg gta gaa aag cag gat caa tcc cct tca tta agg act gga   1251
Lys Pro Met Val Glu Lys Gln Asp Gln Ser Pro Ser Leu Arg Thr Gly
    395                 400                 405 gaa gaa aaa aaa gac gtg tcc att tcc aga ctg cga gag gcc ttt tct   1299
Glu Glu Lys Lys Asp Val Ser Ile Ser Arg Leu Arg Glu Ala Phe Ser
410                 415                 420                 425 ctt cgt cac aca aca gag aac aag cct cac agc cca aag act cca gaa   1347
Leu Arg His Thr Thr Glu Asn Lys Pro His Ser Pro Lys Thr Pro Glu
            430                 435                 440 cca aga agg agc cct cta gga cag aaa agg ggt atg ctg tct tct agc   1395
Pro Arg Arg Ser Pro Leu Gly Gln Lys Arg Gly Met Leu Ser Ser Ser
        445                 450                 455 act tca ggt gcc atc tct gac aaa ggc gtc ctg aga cct cag aaa gag   1443
Thr Ser Gly Ala Ile Ser Asp Lys Gly Val Leu Arg Pro Gln Lys Glu
        460                 465                 470 gca gtg agt tcc agt cac gga ccc agt gac cct acg gac aga gcg gag   1491
Ala Val Ser Ser Ser His Gly Pro Ser Asp Pro Thr Asp Arg Ala Glu
475                 480                 485 gtg gag aag gac tcg ggg cac ggc agc act tcc gtg gat tct gag ggg   1539
Val Glu Lys Asp Ser Gly His Gly Ser Thr Ser Val Asp Ser Glu Gly
490                 495                 500                 505 ttc agc atc cca gac acg ggc agt cac tgc agc agc gag tat gcg gcc   1587
Phe Ser Ile Pro Asp Thr Gly Ser His Cys Ser Ser Glu Tyr Ala Ala
            510                 515                 520 agc tcc cca ggg gac agg ggc tcg cag gaa cat gtg gac tct cag gag   1635
Ser Ser Pro Gly Asp Arg Gly Ser Gln Glu His Val Asp Ser Gln Glu
        525                 530                 535 aaa gcg cct gaa act gac gac tct ttt tca gat gtg gac tgc cat tca   1683
Lys Ala Pro Glu Thr Asp Asp Ser Phe Ser Asp Val Asp Cys His Ser
        540                 545                 550 aac cag gaa gat acc gga tgt aaa ttt cga gtt ttg cct cag cca act   1731
Asn Gln Glu Asp Thr Gly Cys Lys Phe Arg Val Leu Pro Gln Pro Thr
555                 560                 565
```

```
aat ctc gca acc cca aac aca aag cgt ttt aaa aaa gaa gaa att ctt    1779
Asn Leu Ala Thr Pro Asn Thr Lys Arg Phe Lys Lys Glu Glu Ile Leu
570                 575                 580                 585 tcc agt tct gac att tgt caa aag tta gta aat act cag gac atg tca    1827
Ser Ser Ser Asp Ile Cys Gln Lys Leu Val Asn Thr Gln Asp Met Ser
                590                 595                 600 gcc tct cag gtt gat gta gct gtg aaa att aat aag aaa gtt gtg ccc    1875
Ala Ser Gln Val Asp Val Ala Val Lys Ile Asn Lys Lys Val Val Pro
            605                 610                 615 ctg gac ttt tct atg agt tct tta gct aaa cga ata aag cag tta cat    1923
Leu Asp Phe Ser Met Ser Ser Leu Ala Lys Arg Ile Lys Gln Leu His
        620                 625                 630 cat gaa gca cag caa agt gaa ggg gaa cag aat tac agg aag ttt agg    1971
His Glu Ala Gln Gln Ser Glu Gly Glu Gln Asn Tyr Arg Lys Phe Arg
    635                 640                 645 gca aag att tgt cct gga gaa aat caa gca gcc gaa gat gaa cta aga    2019
Ala Lys Ile Cys Pro Gly Glu Asn Gln Ala Ala Glu Asp Glu Leu Arg
650                 655                 660                 665 aaa gag ata agt aaa acg atg ttt gca gaa atg gaa atc att ggt cag    2067
Lys Glu Ile Ser Lys Thr Met Phe Ala Glu Met Glu Ile Ile Gly Gln
                670                 675                 680 ttt aac ctg gga ttt ata ata acc aaa ctg aat gag gat atc ttc ata    2115
Phe Asn Leu Gly Phe Ile Ile Thr Lys Leu Asn Glu Asp Ile Phe Ile
            685                 690                 695 gtg gac cag cat gcc acg gac gag aag tat aac ttc gag atg ctg cag    2163
Val Asp Gln His Ala Thr Asp Glu Lys Tyr Asn Phe Glu Met Leu Gln
        700                 705                 710 cag cac acc gtg ctc cag ggg cag agg ctc ata gca cct cag act ctc    2211
Gln His Thr Val Leu Gln Gly Gln Arg Leu Ile Ala Pro Gln Thr Leu
    715                 720                 725 aac tta act gct gtt aat gaa gct gtt ctg ata gaa aat ctg gaa ata    2259
Asn Leu Thr Ala Val Asn Glu Ala Val Leu Ile Glu Asn Leu Glu Ile
730                 735                 740                 745 ttt aga aag aat ggc ttt gat ttt gtt atc gat gaa aat gct cca gtc    2307
Phe Arg Lys Asn Gly Phe Asp Phe Val Ile Asp Glu Asn Ala Pro Val
                750                 755                 760 act gaa agg gct aaa ctg att tcc ttg cca act agt aaa aac tgg acc    2355
Thr Glu Arg Ala Lys Leu Ile Ser Leu Pro Thr Ser Lys Asn Trp Thr
            765                 770                 775 ttc gga ccc cag gac gtc gat gaa ctg atc ttc atg ctg agc gac agc    2403
Phe Gly Pro Gln Asp Val Asp Glu Leu Ile Phe Met Leu Ser Asp Ser
        780                 785                 790 cct ggg gtc atg tgc cgg cct tcc cga gtc aag cag atg ttt gcc tcc    2451
Pro Gly Val Met Cys Arg Pro Ser Arg Val Lys Gln Met Phe Ala Ser
    795                 800                 805 aga gcc tgc cgg aag tcg gtg atg att ggg act gct ctt aac aca agc    2499
Arg Ala Cys Arg Lys Ser Val Met Ile Gly Thr Ala Leu Asn Thr Ser
810                 815                 820                 825 gag atg aag aaa ctg atc acc cac atg ggg gag atg gac cac ccc tgg    2547
Glu Met Lys Lys Leu Ile Thr His Met Gly Glu Met Asp His Pro Trp
                830                 835                 840 aac tgt ccc cat gga agg cca acc atg aga cac atc gcc aac ctg ggt    2595
Asn Cys Pro His Gly Arg Pro Thr Met Arg His Ile Ala Asn Leu Gly
            845                 850                 855 gtc att tct cag aac tgaccgtagt cactgtatgg aataattggt tttatcgcag    2650
Val Ile Ser Gln Asn
        860 atttttatgt tttgaaagac agagtcttca ctaaccttttt tgttttaaa atgaaacctg    2710
```

-continued

```
ctacttaaaa aaaatacaca tcacacccat ttaaaagtga tcttgagaac cttttcaaac    2770
c                                                                  2771
```

<210> SEQ ID NO 2
<211> LENGTH: 862
<212> TYPE: PRT
<213> ORGANISM: Homo sapiens

<400> SEQUENCE: 2

```
Met Glu Arg Ala Glu Ser Ser Thr Glu Pro Ala Lys Ala Ile Lys
 1               5                  10                  15

Pro Ile Asp Arg Lys Ser Val His Gln Ile Cys Ser Gly Gln Val Val
            20                  25                  30

Leu Ser Leu Ser Thr Ala Val Lys Glu Leu Val Glu Asn Ser Leu Asp
        35                  40                  45

Ala Gly Ala Thr Asn Ile Asp Leu Lys Leu Lys Asp Tyr Gly Val Asp
    50                  55                  60

Leu Ile Glu Val Ser Asp Asn Gly Cys Gly Val Glu Glu Asn Phe
65                  70                  75                  80

Glu Gly Leu Thr Leu Lys His His Thr Ser Lys Ile Gln Glu Phe Ala
                85                  90                  95

Asp Leu Thr Gln Val Glu Thr Phe Gly Phe Arg Gly Glu Ala Leu Ser
            100                 105                 110

Ser Leu Cys Ala Leu Ser Asp Val Thr Ile Ser Thr Cys His Ala Ser
        115                 120                 125

Ala Lys Val Gly Thr Arg Leu Met Phe Asp His Asn Gly Lys Ile Ile
    130                 135                 140

Gln Lys Thr Pro Tyr Pro Arg Pro Arg Gly Thr Thr Val Ser Val Gln
145                 150                 155                 160

Gln Leu Phe Ser Thr Leu Pro Val Arg His Lys Glu Phe Gln Arg Asn
                165                 170                 175

Ile Lys Lys Glu Tyr Ala Lys Met Val Gln Val Leu His Ala Tyr Cys
            180                 185                 190

Ile Ile Ser Ala Gly Ile Arg Val Ser Cys Thr Asn Gln Leu Gly Gln
        195                 200                 205

Gly Lys Arg Gln Pro Val Val Cys Thr Gly Gly Ser Pro Ser Ile Lys
    210                 215                 220

Glu Asn Ile Gly Ser Val Phe Gly Gln Lys Gln Leu Gln Ser Leu Ile
225                 230                 235                 240

Pro Phe Val Gln Leu Pro Pro Ser Asp Ser Val Cys Glu Glu Tyr Gly
                245                 250                 255

Leu Ser Cys Ser Asp Ala Leu His Asn Leu Phe Tyr Ile Ser Gly Phe
            260                 265                 270

Ile Ser Gln Cys Thr His Gly Val Gly Arg Ser Ser Thr Asp Arg Gln
        275                 280                 285

Phe Phe Phe Ile Asn Arg Arg Pro Cys Asp Pro Ala Lys Val Cys Arg
    290                 295                 300

Leu Val Asn Glu Val Tyr His Met Tyr Asn Arg His Gln Tyr Pro Phe
305                 310                 315                 320

Val Val Leu Asn Ile Ser Val Asp Ser Glu Cys Val Asp Ile Asn Val
                325                 330                 335

Thr Pro Asp Lys Arg Gln Ile Leu Leu Gln Glu Glu Lys Leu Leu Leu
            340                 345                 350

Ala Val Leu Lys Thr Ser Leu Ile Gly Met Phe Asp Ser Asp Val Asn
```

```
            355                 360                 365
Lys Leu Asn Val Ser Gln Gln Pro Leu Leu Asp Val Glu Gly Asn Leu
            370                 375                 380
Ile Lys Met His Ala Ala Asp Leu Glu Lys Pro Met Val Glu Lys Gln
385                 390                 395                 400
Asp Gln Ser Pro Ser Leu Arg Thr Gly Glu Glu Lys Lys Asp Val Ser
            405                 410                 415
Ile Ser Arg Leu Arg Glu Ala Phe Ser Leu Arg His Thr Thr Glu Asn
            420                 425                 430
Lys Pro His Ser Pro Lys Thr Pro Glu Pro Arg Arg Ser Pro Leu Gly
            435                 440                 445
Gln Lys Arg Gly Met Leu Ser Ser Ser Thr Ser Gly Ala Ile Ser Asp
            450                 455                 460
Lys Gly Val Leu Arg Pro Gln Lys Glu Ala Val Ser Ser Ser His Gly
465                 470                 475                 480
Pro Ser Asp Pro Thr Asp Arg Ala Glu Val Glu Lys Asp Ser Gly His
                    485                 490                 495
Gly Ser Thr Ser Val Asp Ser Glu Gly Phe Ser Ile Pro Asp Thr Gly
                500                 505                 510
Ser His Cys Ser Ser Glu Tyr Ala Ala Ser Ser Pro Gly Asp Arg Gly
            515                 520                 525
Ser Gln Glu His Val Asp Ser Gln Glu Lys Ala Pro Glu Thr Asp Asp
            530                 535                 540
Ser Phe Ser Asp Val Asp Cys His Ser Asn Gln Glu Asp Thr Gly Cys
545                 550                 555                 560
Lys Phe Arg Val Leu Pro Gln Pro Thr Asn Leu Ala Thr Pro Asn Thr
                565                 570                 575
Lys Arg Phe Lys Lys Glu Glu Ile Leu Ser Ser Ser Asp Ile Cys Gln
            580                 585                 590
Lys Leu Val Asn Thr Gln Asp Met Ser Ala Ser Gln Val Asp Val Ala
            595                 600                 605
Val Lys Ile Asn Lys Lys Val Val Pro Leu Asp Phe Ser Met Ser Ser
        610                 615                 620
Leu Ala Lys Arg Ile Lys Gln Leu His His Glu Ala Gln Gln Ser Glu
625                 630                 635                 640
Gly Glu Gln Asn Tyr Arg Lys Phe Arg Ala Lys Ile Cys Pro Gly Glu
                645                 650                 655
Asn Gln Ala Ala Glu Asp Glu Leu Arg Lys Glu Ile Ser Lys Thr Met
            660                 665                 670
Phe Ala Glu Met Glu Ile Ile Gly Gln Phe Asn Leu Gly Phe Ile Ile
            675                 680                 685
Thr Lys Leu Asn Glu Asp Ile Phe Ile Val Asp Gln His Ala Thr Asp
        690                 695                 700
Glu Lys Tyr Asn Phe Glu Met Leu Gln Gln His Thr Val Leu Gln Gly
705                 710                 715                 720
Gln Arg Leu Ile Ala Pro Gln Thr Leu Asn Leu Thr Ala Val Asn Glu
                725                 730                 735
Ala Val Leu Ile Glu Asn Leu Glu Ile Phe Arg Lys Asn Gly Phe Asp
                740                 745                 750
Phe Val Ile Asp Glu Asn Ala Pro Val Thr Glu Arg Ala Lys Leu Ile
            755                 760                 765
Ser Leu Pro Thr Ser Lys Asn Trp Thr Phe Gly Pro Gln Asp Val Asp
        770                 775                 780
```

-continued

```
Glu Leu Ile Phe Met Leu Ser Asp Ser Pro Gly Val Met Cys Arg Pro
785                 790                 795                 800

Ser Arg Val Lys Gln Met Phe Ala Ser Arg Ala Cys Arg Lys Ser Val
            805                 810                 815

Met Ile Gly Thr Ala Leu Asn Thr Ser Glu Met Lys Lys Leu Ile Thr
        820                 825                 830

His Met Gly Glu Met Asp His Pro Trp Asn Cys Pro His Gly Arg Pro
    835                 840                 845

Thr Met Arg His Ile Ala Asn Leu Gly Val Ile Ser Gln Asn
850                 855                 860

<210> SEQ ID NO 3
<211> LENGTH: 52
<212> TYPE: DNA
<213> ORGANISM: Homo sapiens

<400> SEQUENCE: 3
ggatcctaat acgactcact agggagac accatgtcg ttcgtggcag gg            52

<210> SEQ ID NO 4
<211> LENGTH: 21
<212> TYPE: DNA
<213> ORGANISM: Homo sapiens

<400> SEQUENCE: 4
taagtcttaa gtgctaccaa c                                            21

<210> SEQ ID NO 5
<211> LENGTH: 18
<212> TYPE: DNA
<213> ORGANISM: Homo sapiens

<400> SEQUENCE: 5
atggagcgag ctgagagc                                                18

<210> SEQ ID NO 6
<211> LENGTH: 20
<212> TYPE: DNA
<213> ORGANISM: Homo sapiens

<400> SEQUENCE: 6
aggttagtga agactctgtc                                              20

<210> SEQ ID NO 7
<211> LENGTH: 19
<212> TYPE: DNA
<213> ORGANISM: Homo sapiens

<400> SEQUENCE: 7
agtcgagttc caaccttcg                                               19

<210> SEQ ID NO 8
<211> LENGTH: 54
<212> TYPE: DNA
<213> ORGANISM: Homo sapiens

<400> SEQUENCE: 8
ggatcctaat acgactcact agggagac accatgatg tttgatcaca atgg          54
```

US 7,829,338 B2

METHOD FOR GENERATING HYPERMUTABLE ORGANISMS

This invention was made using a U.S. government grant from the NIH (CA43460). Therefore, the U.S. government retains certain rights to the invention.

TECHNICAL FIELD OF THE INVENTION

The invention is related to the area of mismatch repair genes. In particular it is related to the field of mutagenesis.

BACKGROUND OF THE INVENTION

Within the past four years, the genetic cause of the Hereditary Nonpolyposis Colorectal Cancer Syndrome (HNPCC), also known as Lynch syndrome II, has been ascertained for the majority of kindreds affected with the disease (13). The molecular basis of HNPCC involves genetic instability resulting from defective mismatch repair (MMR). To date, six genes have been identified in humans that encode for proteins and appear to participate in the MMR process, including the mutS homologs GTBP, hMSH2, and hMSH3 and the mutL homologs hMLH1, hPMS1, and hPMS2 (2, 7, 11, 17, 20, 21, 22, 24). Germline mutations in four of these genes (hMSH2, hMLH1, hPMS1, and hPMS2) have been identified in HNPCC kindreds (2, 11, 13, 17, 24). Though the mutator defect that arises from the MMR deficiency can affect any DNA sequence, microsatellite sequences are particularly sensitive to MMR abnormalities (14). Microsatellite instability is therefore a useful indicator of defective MMR. In addition to its occurrence in virtually all tumors arising in HNPCC patients, Microsatellite instability is found in a small fraction of sporadic tumors with distinctive molecular and phenotypic properties (27).

HNPCC is inherited in an autosomal dominant fashion, so that the normal cells of affected family members contain one mutant allele of the relevant MMR gene (inherited from an affected parent) and one wild-type allele (inherited from the unaffected parent). During the early stages of tumor development, however, the wild-type allele is inactivated through a somatic mutation, leaving the cell with no functional MMR gene and resulting in a profound defect in MMR activity. Because a somatic mutation in addition to a germ-line mutation is required to generate defective MMR in the tumor cells, this mechanism is generally referred to as one involving "two hits," analogous to the biallelic inactivation of tumor suppressor genes that initiate other hereditary cancers (11, 13, 25). In line with this two-hit mechanism, the non-neoplastic cells of HNPCC patients generally retain near normal levels of MMR activity due to the presence of the wild-type allele.

SUMMARY OF THE INVENTION

It is an object of the present invention to provide a method for rendering cells hypermutable.

It is another object of the present invention to provide genetically altered cell lines.

It is yet another object of the present invention to provide a method to produce transgenic animals that are hypermutable.

It is also an object of the present invention to provide genetically altered transgenic animals.

It is a further object of the invention to provide a method of mutating a gene of interest in a cell.

Yet another object of the invention is to provide a method of mutating a gene of interest in an animal.

These and other objects of the invention are provided by one or more of the embodiments described below. In one embodiment of the invention, a method for making a hypermutable cell is provided. A polynucleotide encoding a dominant negative allele of a mismatch repair gene is introduced into a cell. The cell becomes hypermutable as a result of the introduction of the gene.

In another embodiment of the invention, an isolated hypermutable cell is provided. The cell comprises a dominant negative allele of a mismatch repair gene.

In another embodiment of the invention, a hypermutable transgenic animal is provided. The animal comprises a dominant negative allele of a mismatch repair gene.

In another embodiment of the invention, a method is provided for introducing a mutation into a gene of interest. A polynucleotide encoding a dominant negative allele of a mismatch repair gene is introduced into a cell. The cell becomes hypermutable as a result of the introduction of the gene. The cell further comprises a gene of interest. The cell is grown. The cell is tested to determine whether the gene of interest harbors a mutation.

In another embodiment of the invention, a method is provided for generating a mutation in a gene of interest. A transgenic animal comprising a polynucleotide encoding a dominant negative allele of a mismatch repair gene is grown. The animal comprises a gene of interest. The animal is tested to determine whether the gene of interest harbors a mutation.

These and other embodiments of the invention provide the art with methods that can generate enhanced mutability in cells and animals as well as providing cells and animals harboring potentially useful mutations.

BRIEF DESCRIPTION OF THE DRAWINGS

FIG. 2. SH cells co-transfected with pCAR reporters and PMS2 expression vectors after 17 days of drug selection.

FIG. 4. Protein expression and β-galactosidase activity in stably transduced SH clones.

FIG. 5. Immunoprecipitation of in vitro translated hPMS2 and hMLH1 proteins. (FIG. 5A) Labelled (indicated by an asterisk) or unlabelled proteins were incubated with an antibody to the C-terminus of hPMS2 in lanes 1-3 and to hMLH1 in lanes 4-6. Lane 7 contains a nonprogrammed reticulocyte lysate. The PMS-135 contains codons 135-862 of hPMS2. The major translation products of hPMS2 and hMLH1 are indicated. (FIG. 5B) Labelled hPMS-134 (containing codons 1-134 of hPMS2) was incubated in the presence or absence of unlabelled HMLH1 plus an antibody to hMLH1 (lanes 1 and 2, respectively). Lane 3 contains lysate from a nonprogrammed reticulolysate. (FIG. 5C) Labelled proteins were incubated with an antibody to the N-terminus of hPMS2. Lane 6 contains a nonprogrammed reticulocyte lysate. In both FIG. 5A and FIG. 5B, autoradiographs of immunoprecipitated products are shown.

FIG. 6. Complementation of MMR activity in transduced SH cells. Lysates from pooled clones stably transduced with PMS2-NOT, PMS2-WT, or PMS2-134 were complemented with purified MutSα or MutLα MMR components using the 5'G/T heteroduplex substrate. The values are presented as the percentage of repair activity in each case compared to that in lysates complemented with both purified MutLα and MutSα components to normalize for repair efficiency in the different lysate backgrounds. The values shown represent the average of at least three different determinations.

DETAILED DESCRIPTION OF THE INVENTION

Figure 1A:
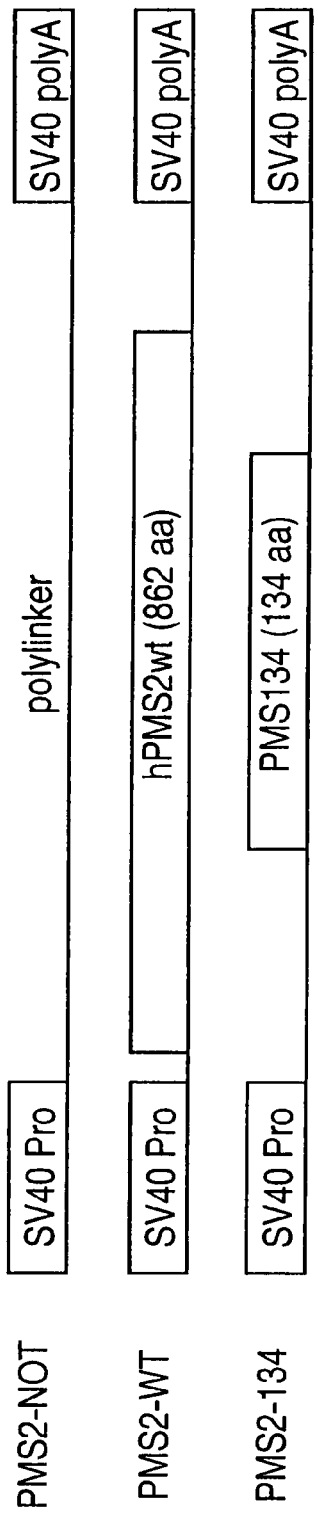
FIG. 1. Diagrams of PMS2 expression vectors (FIG. 1A) and pCAR reporters (FIG. 1B).

The inventors have discovered a method for developing hypermutable cells and animals by taking advantage of newly discovered alleles of human mismatch repair genes. Dominant negative alleles of such genes, when introduced into cells or transgenic animals, increase the rate of spontaneous mutations by reducing the effectiveness of DNA repair and thereby render the cells or animals hypermutable. Hypermutable cells or animals can then be utilized to develop new mutations in a gene of interest.

The process of mismatch repair, also called mismatch proofreading, is carried out by protein complexes in cells ranging from bacteria to mammalian cells. A mismatch repair gene is a gene that encodes one of the proteins of such a mismatch repair complex. Although not wanting to be bound by any particular theory of mechanism of action, a mismatch repair complex is believed to detect distortions of the DNA helix resulting from non-complementary pairing of nucleotide bases. The non-complementary base on the newer DNA strand is excised, and the excised base is replaced with the appropriate base which is complementary to the older DNA strand. In this way, cells eliminate many mutations which occur as a result of mistakes in DNA replication.

Dominant negative alleles cause a mismatch repair defective phenotype even in the presence of a wild-type allele in the same cell. An example of a dominant negative allele of a mismatch repair gene is the human gene hPMS2-134, which carries a truncation mutation at codon 134. The mutation causes the product of this gene to abnormally terminate at the position of the 134th amino acid, resulting in a shortened polypeptide containing the N-terminal 133 amino acids. Such a mutation causes an increase in the rate of mutations which accumulate in cells after DNA replication. Expression of a dominant negative allele of a mismatch repair gene results in impairment of mismatch repair activity, even in the presence of the wild-type allele. Any allele which produces such effect can be used in this invention.

Dominant negative alleles of a mismatch repair gene can be obtained from the cells of humans, animals, yeast, bacteria, or other organisms. Such alleles can be identified by screening cells for defective mismatch repair activity. The cells may be mutagenized or not. Cells from animals or humans with cancer can be screened for defective mismatch repair. Cells from colon cancer patients may be particularly useful. Genomic DNA, cDNA, or mRNA from any cell encoding a mismatch repair protein can be analyzed for variations from the wild type sequence. Dominant negative alleles of a mismatch repair gene can also be created artificially, for example, by producing variants of the hPMS2-134 allele or other mismatch repair genes. Various techniques of site-directed mutagenesis can be used. The suitability of such alleles, whether natural or artificial, for use in generating hypermutable cells or animals can be evaluated by testing the mismatch repair activity caused by the allele in the presence of one or more wild-type alleles, to determine if it is a dominant negative allele.

A cell or an animal into which a dominant negative allele of a mismatch repair gene has been introduced will become hypermutable. This means that the spontaneous mutation rate of such cells or animals is elevated compared to cells or animals without such alleles. The degree of elevation of the spontaneous mutation rate can be at least 2-fold, 5-fold, 10-fold, 20-fold, 50-fold, 100-fold, 200-fold, 500-fold, or 1000-fold that of the normal cell or animal.

According to one aspect of the invention, a polynucleotide encoding a dominant negative form of a mismatch repair protein is introduced into a cell or a transgenic animal. The gene can be any dominant negative allele encoding a protein which is part of a mismatch repair complex, for example, PMS2, PMS1, MLH1, or MSH2. The dominant negative allele can be naturally occurring or made in the laboratory. The polynucleotide can be in the form of genomic DNA, cDNA, RNA, or a chemically synthesized polynucleotide. The polynucleotide can be introduced into the cell by transfection.

Transfection is any process whereby a polynucleotide is introduced into a cell. The process of transfection can be carried out in a living animal, e.g., using a vector for gene therapy, or it can be carried out in vitro, e.g., using a suspension of one or more isolated cells in culture. The cell can be any type of eukaryotic cell, including, for example, cells isolated from humans or other primates, mammals or other vertebrates, invertebrates, and single celled organisms such as protozoa or yeast.

In general, transfection will be carried out using a suspension of cells, or a single cell, but other methods can also be applied as long as a sufficient fraction of the treated cells or tissue incorporates the polynucleotide so as to allow transfected cells to be grown and utilized. The protein product of the polynucleotide may be transiently or stably expressed in the cell. Techniques for transfection are well known. Available techniques for introducing polynucleotides include but are not limited to electroporation, transduction, cell fusion, the use of calcium chloride, and packaging of the polynucleotide together with lipid for fusion with the cells of interest. Once a cell has been transfected with the mismatch repair gene, the cell can be grown and reproduced in culture. If the transfection is stable, such that the gene is expressed at a consistent level for many cell generations, then a cell line results.

An isolated cell is a cell obtained from a tissue of humans or animals by mechanically separating out individual cells and transferring them to a suitable cell culture medium, either with or without pretreatment of the tissue with enzymes, e.g., collagenase or trypsin. Such isolated cells are typically cultured in the absence of other types of cells. Cells selected for the introduction of a dominant negative allele of a mismatch repair gene may be derived from a eukaryotic organism in the form of a primary cell culture or an immortalized cell line, or may be derived from suspensions of single-celled organisms.

A polynucleotide encoding a dominant negative form of a mismatch repair protein can be introduced into the genome of an animal by producing a transgenic animal. The animal can be any species for which suitable techniques are available to produce transgenic animals. For example, transgenic animals can be prepared from domestic livestock, e.g., cows, pigs, sheep, goats, horses, etc.; from animals used for the production of recombinant proteins, e.g., cows, pigs, or goats that express a recombinant protein in their milk; or experimental animals for research or product testing, e.g., mice, rats, hamsters, guinea pigs, rabbits, etc.

Any method for making transgenic animals known in the art can be used. According to one process of producing a transgenic animal, the polynucleotide is injected into a fertilized egg of the animal and the injected egg is placed into a pseudo-pregnant female. The egg develops into a mature animal in which the polynucleotide is incorporated and expressed. The fertilized egg is produced in vitro from the egg and sperm of donor animals of the same species as the pseudo-pregnant female, who is prepared by hormone treatments to receive the fertilized egg and become pregnant. An alternative method for producing transgenic animals involves introducing the polynucleotide into embryonic cells by injection or transfection and reintroducing the embryonic cells into the developing embryo. With this method, however, if the polynucleotide is not incorporated into germline cells, the gene will not be passed on to the progeny. Therefore, a transgenic animal produced by this method must be evaluated to determine whether the gene is incorporated into germ cells of the animal. Once transgenic animals are produced, they can be grown to reproductive age, when they can be mated to produce and maintain a colony of transgenic animals.

Once a transfected cell line or a colony of transgenic animals has being produced, it can be used to generate new mutations in one or more gene(s) of interest. A gene of interest can be any gene naturally possessed by the cell line or transgenic animal or introduced into the cell line or transgenic animal. An advantage of using such cells or animals to induce mutations is that the cell or animal need not be exposed to mutagenic chemicals or radiation, which may have secondary harmful effects, both on the object of the exposure and on the workers.

Mutations can be detected by analyzing for alterations in the genotype of the cells or animals, for example by examining the sequence of genomic DNA, cDNA, messenger RNA, or amino acids associated with the gene of interest. Mutations can also be detected by screening the phenotype of the gene. A mutant phenotype can be detected by identifying alterations in electrophoretic mobility, spectroscopic properties, or other physical or structural characteristics of a protein encoded by a mutant gene. One can also screen for altered function of the protein in situ, in isolated form, or in model systems. One can screen for alteration of any property of the cell or animal associated with the function of the gene of interest.

The above disclosure generally describes the present invention. A more complete understanding can be obtained by reference to the following specific examples which are provided herein for purposes of illustration only, and are not intended to limit the scope of the invention.

EXAMPLE 1 hPMS2-134 Encodes a Dominant Negative Mismatch Repair Protein

A profound defect in MMR was found in the normal cells of two HNPCC patients. That this defect was operative in vivo was demonstrated by the widespread presence of microsatellite instability in non-neoplastic cells of such patients. One of the two patients had a germ-line truncating mutation of the hPMS2 gene at codon 134 (the hPMS2-134 mutation), while the other patient had a small germ-line deletion within the hMLH1 gene (26). These data thus contradicted the two-hit model generally believed to explain the biochemical and biological features of HNPCC patients. The basis for this MMR deficiency in the normal cells of these patients was nuclear, and several potential explanations were offered. For example, it was possible that the second allele of the relevant MMR gene was inactivated in the germ-line of these patients through an undiscovered mechanism, or that unknown mutations of other genes involved in the MMR process were present that cooperated with the known germ-line mutation. It is clear from knock-out experiments in mice that MMR-deficiency is compatible with normal growth and development, supporting these possibilities (1, 3, 6). Alternatively, it was possible that the mutant alleles exerted a dominant negative effect, resulting in MMR deficiency even in the presence of the wild-type allele of the corresponding MMR gene and all other genes involved in the MMR process. To distinguish between these possibilities, we expressed the truncated polypeptide encoded by the hPMS2-134 mutation in an MMR proficient cell line and analyzed its affect on the cell's MMR activity. The results showed that this mutant could indeed exert a dominant negative effect, resulting in biochemical and genetic manifestations of MMR deficiency.

Figure 1B:
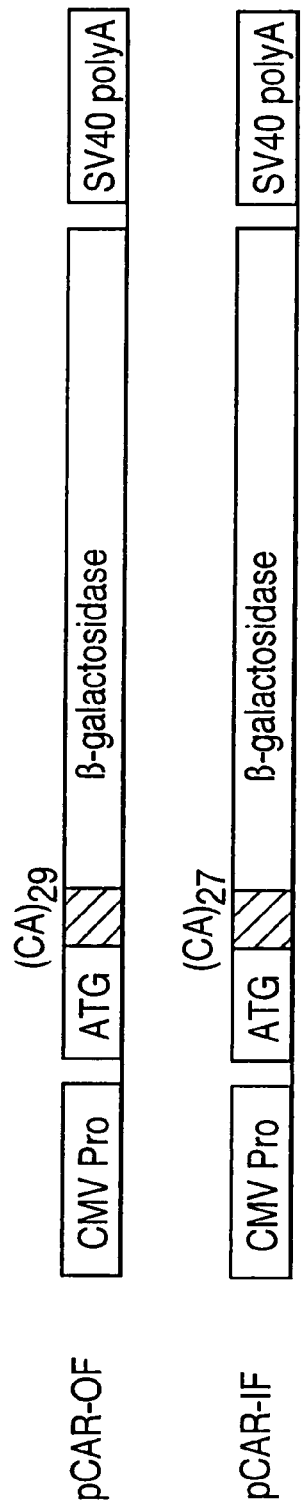

The MMR proficient Syrian hamster TK⁻ts 13 cell line (hereafter called SH cells) was cotransfected with various hPMS2 expression plasmids plus reporter constructs for assessing MMR activity. The hPMS2 expression plasmids contained the normal hPMS2 gene product or the truncated hPMS2 gene identified in the patient described above (PMS2-WT and PMS2-134, respectively, FIG. 1A). An "empty" vector devoid of hPMS2 sequences (PMS2-NOT, FIG. 1A) served as an additional control. The reporter construct pCAR-OF (out of frame) contained a hygromycin resistance gene plus a β-galactosidase gene containing a 29 bp out-of-frame poly-CA tract at the 5' end of its coding region. The reporter construct pCAR-IF (in frame) was identical except that the poly-CA tract was 27 bp and therefore did not disrupt the β-galactosidase reading frame (FIG. 1B). The pCAR-OF reporter would not generate β-galactosidase activity unless a frame-restoring mutation (i.e., insertion or deletion) arose following transfection.

Figure 2A:
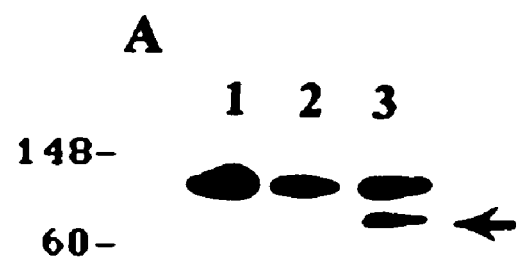
(FIG. 2A) Western blots of lysates from untransfected SH cells (lane 1) or SH cells transfected with PMS2-NOT (lane 2) or PMS2-WT (lane 3). The arrow indicates the 110 kD protein expected for hPMS2.
Figure 2B:
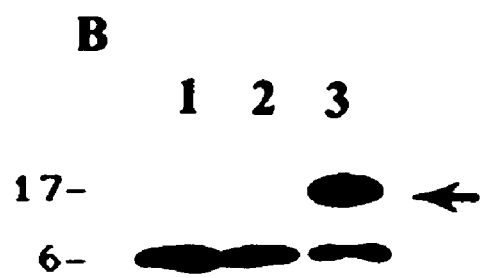
(FIG. 2B) Western blots of lysates from untransfected SH cells (lane 1) or SH cells transfected with PMS2-NOT (lane 2) or PMS2-134 (lane 3). The arrow indicates the 14 kD protein expected for hPMS-134. Both A and B were probed with an antibody generated against the N-terminus of hPMS2. The upper polypeptides in A and the lower polypeptides in B represent cross-reactive hamster proteins.
Figure 2C:
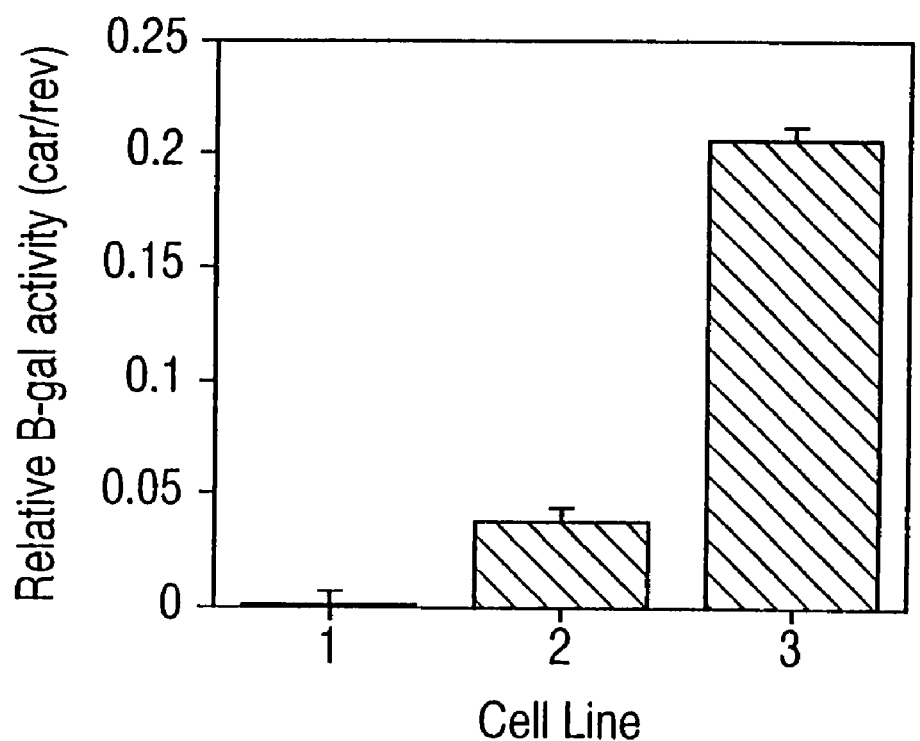
(FIG. 2C) β-galactosidase activity in lysates derived from SH cells co-transfected with PMS2-NOT (lane 1), PMS2-WT (lane 2), or PMS2-134 (lane 3) plus reporter plasmid. Relative β-galactosidase activities are defined as the ratio of β-galactosidase activity in cells transfected with pCAR-OF compared to that in cells transfected with pCAR-IF; this normalization controlled for transfection efficiency and controlled for β-galactosidase activity in the cells expressing the various PMS2 effector genes.
Figure 3A:
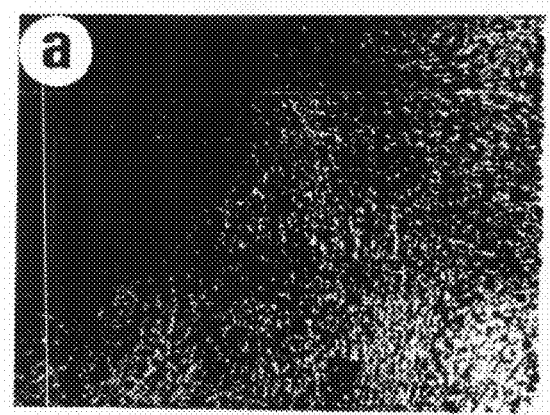
FIG. 3. In situ β-galactosidase activity of pooled clones of SH cells stably transduced with the PMS2-NOT (FIG. 3A), PMS2-WT (FIG. 3B), or PMS2-134 (FIG. 3C) expression vectors, then re-transfected with pCAR-OF reporter. After 17 days of drug selection, the colonies were pooled, cultured, and stained for β-galactosidase activity. A pooled culture of PMS2-134 transduced SH cells expressing β-galactosidase from pCAR-OF is visible in FIG. 3C. The level of expression is lower, as expected, than in SH cells transfected with the pCAR-IF reporter plasmid, shown as a positive control in FIG. 3D. Each of the fields illustrated is representative of that found in triplicate experiments.
Figure 3B:
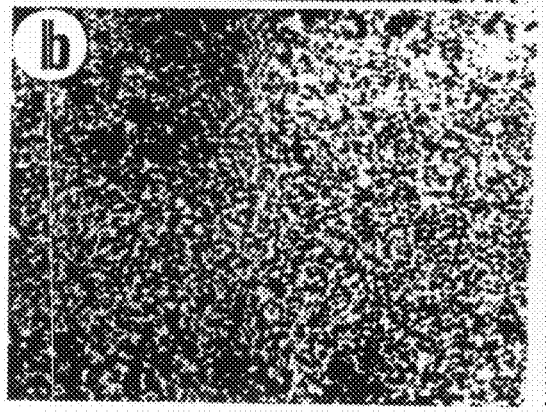
Figure 3C:
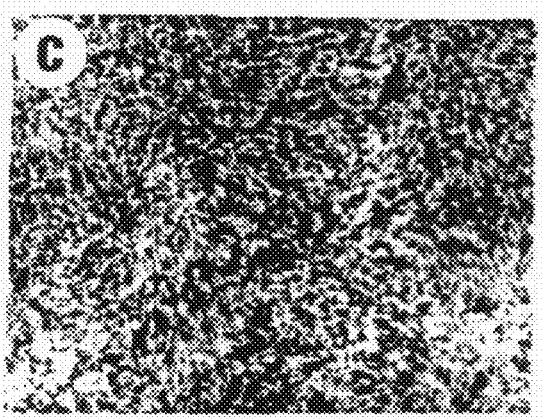
Figure 3D:
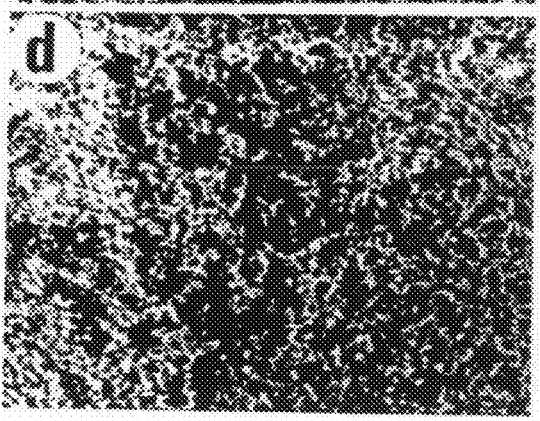

Three different transfection schemes were used to evaluate the effects of the PMS2-134 mutation on SH cells. In the first scheme, the expression vectors plus the reporters were co-transfected together. Pools containing greater than 100 clones were generated following selection with hygromycin for 17 days and harvested for Western blot and β-galactosidase assays. SH cells transduced with PMS2-WT and PMS2-134 synthesized polypeptides of the expected size, as assessed with anti-hPMS2 antibodies on Western blots (FIGS. 2A and 2B). As expected, virtually no β-galactosidase activity was observed in SH cells transfected with the pCAR-OF reporter plus PMS2-NOT (FIG. 2C). However, SH cells transfected with PMS2-134 expressed considerable β-galactosidase activity, significantly more than those transfected with PMS2-WT (FIG. 2C). These results suggested that the truncated polypeptide encoded by the PMS2-134 construct perturbs the endogenous MMR machinery, resulting in deletions or insertions that restored the reading frame. The exact nature of these presumed deletions or insertions could not be assessed, as multiple copies of the reporter constructs were transduced under our conditions, and the wild type β-galactosidase sequence was in great excess over the expected mutants, precluding their demonstration by direct sequencing.

In the second scheme, SH cells were co-transfected with each of the PMS2 expression vectors plus the hygromycin-resistance plasmid pLHL4. Hygromycin resistant cultures containing greater than 100 clones were pooled and expanded. These cultures were then co-transfected with PCAR-IF or pCAR-OF reporters plus a separate plasmid allowing geneticin selection. Two weeks later, the pooled cells, each containing more than 100 colonies resistant to both hygromycin and geneticin, were stained with X-gal to assess β-galactosidase activity. As shown in FIG. 3, the cultures transfected with PMS2-134 (panel C) contained many blue cells, while virtually no cells were blue in the cultures transfected with PMS2-NOT or PMS2-WT (panels A and B, respectively). In each case, transfection efficiency was controlled by parallel transfections using pCAR-IF which also served as a control for β-galactosidase activity of cells expressing the various PMS2 effector genes, which resulted in similar β-galactosidase expression levels in all cases (example in FIG. 3D). Increases in β-galactosidase activity after PMS2-134 transfection compared to PMS2-WT transfection were also observed when a similar experimental protocol was applied to the MMR-proficient human embryonic kidney cell line 293. These cells were cotransfected with the pCAR-OF plus the various PMS2 effector plasmids and selected for 17 days in hygromycin. At day 17, colonies were stained with X-gal to assess β-galactosidase activity and scored for β-galactosidase expressing cells. As shown in Table 1, only those cells expressing the PMS2-134 polypeptide expressed a detectable β-galactosidase activity. These data demonstrate a similar dominant negative effect of the hPMS2-134 protein in both rodent and human systems and validate the utility of the rodent system in these studies.

Figure 4A:
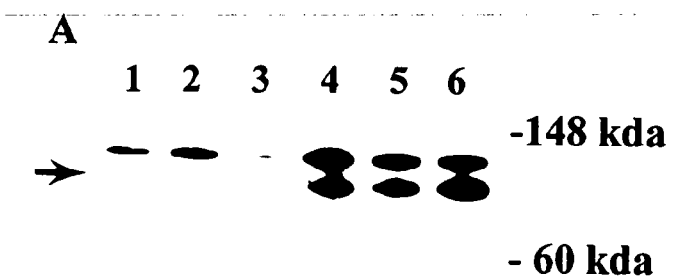
(FIG. 4A) Western blots of lysates from clones stably transduced with PMS2-NOT (lanes 1-3) or PMS2-WT (lanes 4-6).
Figure 4B:
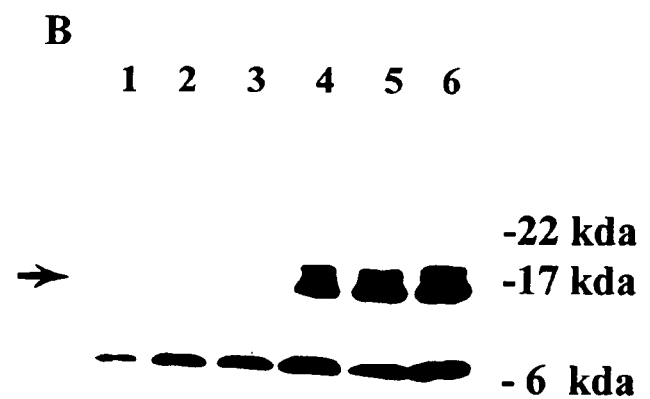
(FIG. 4B) Western blots of lysates from clones stably transduced with PMS2-NOT (lanes 1-3) or PMS2-134 (lanes 4-6). (The arrows indicate the polypeptide of the appropriate molecular weight. The upper (FIG. 4A) and lower (FIG. 4B) molecular weight polypeptides are nonspecific proteins.
Figure 4C:
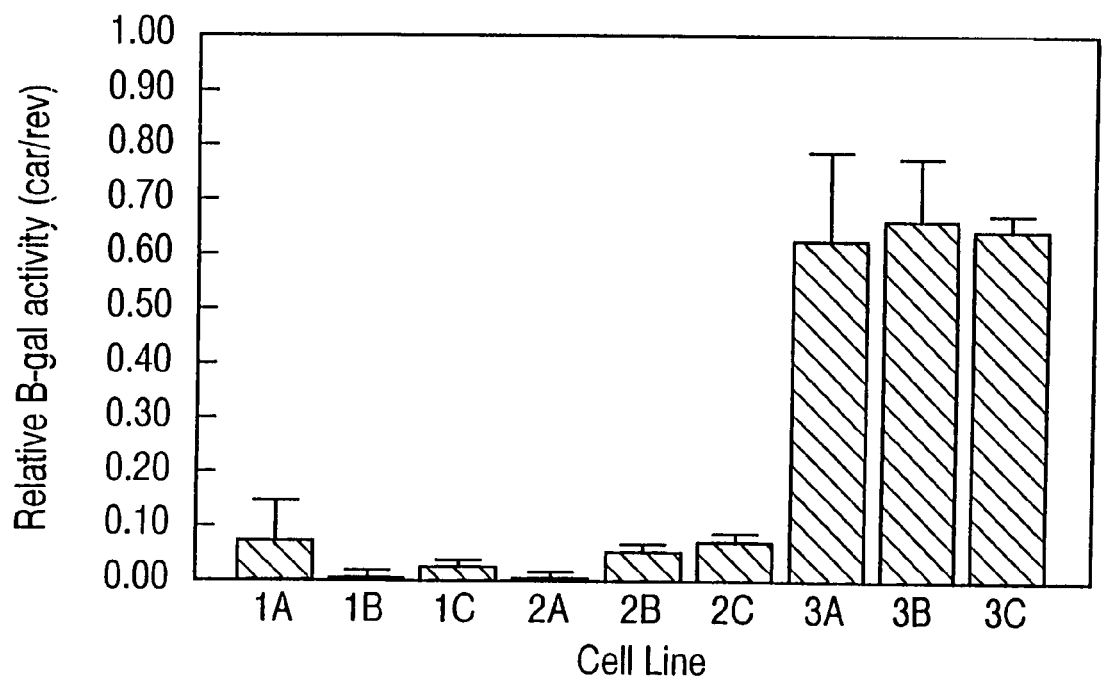
(FIG. 4C) The clones expressing PMS2-NOT (lane 1A-3A), PMS2-WT (lanes 1B-3B), or PMS2-134 (lanes 1C-3C) were transduced with pCAR-OF or pCAR-IF reporter plasmids and multiple subclones selected in hygromycin plus geneticin were harvested 17 days later and assayed for β-galactosidase activity. Relative β-galactosidase activities are defined as the ratio of β-galactosidase activity in cells transduced with pCAR-OF compared to that in cells transduced with pCAR-IF.

In the third scheme, SH cells were transfected with each of the PMS2 expression vectors as described for the second scheme, but individual clones, rather than pooled clones, were expanded following drug selection. Of twenty clones transfected with PMS2-WT, five were shown to express readily detectable levels of full-length PMS2 proteins (examples in FIG. 4A, lanes 4-6). Similar analyses of twenty PMS2-134 clones revealed four clones which expressed truncated PMS2 polypeptides of the expected size (examples in FIG. 4B, lanes 4-6). Three clones expressing full-length or truncated PMS2 proteins, as well as three randomly selected clones from PMS2-NOT transfected cells (FIGS. 4A and 4B, lanes 1-3) were chosen for further analysis. The individual clones were tested for β-galactosidase activity following co-transfection with pCAR-OF plus the PNTK plasmid, as described above for the pooled clones. As shown in FIG. 4C, each of the three clones (lanes 3A-3C) expressing the truncated hPMS2 polypeptide yielded much higher β-galactosidase activities following transfection with pCAR-OF than did the clones expressing the full-length hPMS2 protein (lanes 2A-2C) or no hPMS2 protein (lanes 1A-1C).

Table 1. β-galactosidase expression of 293 clones transfected with pCAR-OF reporter construct plus PMS2 effector plasmids. 293 cells were cotransfected with the pCAR-OF β-galactosidase reporter plasmid plus the PMS2-NOT, -WT, or -134 effector plasmids. Transfected cells were selected in hygromycin for 17 days and stained with x-gal for β-galactosidase activity (blue colored cells). The results below represent the mean+/−standard deviation of triplicate experiments.

| Sample | Blue colonies | White colonies |
| --- | --- | --- |
| PMS2-NOT | 0 +/− 0 | 17 +/− 2.7 |
| PMS2-WT | 0 +/− 0 | 18 +/− 4.0 |
| PMS2-134 | 15 +/− 2.1 | 6 +/− 2.1 |

Plasmids. The full-length wild-type hPMS2 cDNA was obtained from a human Hela cDNA library as described (18). An hPMS2 cDNA containing a termination codon at amino acid 134 was obtained via RT-PCR from the patient in which the mutation was discovered (9). The cDNA fragments were cloned into the BamHI site into the pSG5 vector, which contains an SV40 promoter followed by an SV40 polyadenylation signal (8). The pCAR reporter vectors described in FIG. 1 were constructed as described in ref. 21 and 25.

Cell lines and transfection. Syrian Hamster fibroblast Tk⁻ts 13 cells were obtained from ATCC and cultured as described (15). Stably transfected cell lines expressing hPMS2 were created by cotransfection of the PMS2 expression vectors and the pLHL4 plasmid encoding the hygromycin resistance gene at a ratio of 3:1 (pCAR:pLHL4) and selected with hygromycin. Stably transfected cell lines containing pCAR reporters were generated by co-transfection of pCAR vectors together with either pNTK plasmid encoding the neomycin resistance plasmid or with pLHL4. All transfections were performed using calcium phosphate as previously described (15).

β-galactosidase assay. Seventeen days following transfection with, pCAR, β-galactosidase assays were performed using 20 μg of protein in 45 mM 2-mercaptoethanol, 1 mM $MgCl_2$, 0.1 M $NaPO_4$ and 0.6 mg/ml Chlorophenol red-β-D-galatopyranoside (CPRG, Boehringer Mannheim). Reactions were incubated for 1 hour, terminated by the addition of 0.5 M $Na_2CO_3$, and analyzed by spectrophotometry at 576 nm (16). For in situ β-galactosidase staining, cells were fixed in 1% glutaraldehyde in PBS and incubated in 0.15 M NaCl, 1 mM $MgCl_2$, 3.3 mM $K_4Fe(CN)_6$, 3.3 mM $K_3Fe(CN)_6$, 0.2% X-Gal for 2 hours at 37° C.

EXAMPLE 2 hPMS2-134 Causes a Defect in MMR Activity

The most likely explanation for the differences in β-galactosidase activity between PMS2-WT and PMS2-134 transfected cells was that the PMS2-134 protein disturbed MMR activity, resulting in a higher frequency of mutation within the pCAR-OF reporter and re-establishing the ORF. To directly test the hypothesis that MMR was altered, we employed a biochemical assay for MMR with the individual clones described in FIG. 4. Nuclear extracts were prepared from the clones and incubated with heteroduplex substrates containing either a /CA\ insertion-deletion or a G/T mismatch under conditions described previously. The /CA\ and G/T heteroduplexes were used to test repair from the 3' and 5' directions, respectively. There was a dramatic difference between the PMS2-134 expressing clones and the other clones in these assays (Table 2A). While all clones repaired substrates from the 3' direction (/CA\ heteroduplex), cells expressing the PMS2-134 polypeptide had very little 5' repair activity. A similar directional defect in mismatch repair was evident with pooled clones resulting from PMS2-134 transfection, or when the heteroduplex contained a 2-4 base pair loop, examples of which are shown in Table 2B. A small decrease in MMR activity was observed in the 3'/CA\ PMS2-WT repair assays, perhaps a result of interference in the biochemical assays by overexpression of the PMS2 protein. No significant activity was caused by PMS2-WT in the in situ β-galactosidase assays (FIG. 3; Table 1), a result more likely to reflect the in vivo condition.

TABLE 2

Mismatch repair activity of nuclear extracts from SH clones (A) or pooled cultures (B). The extracts were tested for MMR activity with 24 fmol of heteroduplex.

A. SH clones*

| Cell Line | Repaired substrate (fmol/15 min) | |
|---|---|---|
| | 3' /CA\ | 5' G/T |
| PMS2-NOT | | |
| clone A | 10.2 | 3.5 |
| clone B | 12.7 | 2.9 |
| clone C | 13.5 | 5.5 |
| PMS2-WT | | |
| clone A | 2.8 | 2.2 |
| clone B | 5.7 | 4.8 |
| clone C | 4.7 | 2.9 |
| PMS2-134 | | |
| clone A | 2.5 | 0.0 |
| clone B | 2.4 | 0.0 |
| clone C | 5.0 | 0.5 |

B. Pooled cultures

| Cell Line | Repaired substrate (fmol/15 min) | | | |
|---|---|---|---|---|
| | 3'G/T | 5'G/T | 3'/CTG\ | 5'/CTG\ |
| PMS2-NOT | 2.07 +/− 0.09 | 2.37 +/− 0.37 | 3.45 +/− 1.35 | 2.77 +/− 1.37 |
| PMS2-WT | 1.65 +/− 0.94 | 1.86 +/− 0.57 | 1.13 +/− 0.23 | 1.23 +/− 0.65 |
| PMS2-134 | 0.14 +/− 0.2 | 0.0 +/− 0.0 | 1.31 +/− 0.66 | 0.0 +/− 0.0 |

*These data represent similar results derived from greater than five independent experiments.

Western blots. Equal number of cells were lysed directly in lysis buffer (60 mM Tris, pH 6.8, 2% SDS, 10% glycerol, 0.1 M 2-mercaptoethanol, 0.001% bromophenol blue) and boiled for 5 minutes. Lysate proteins were separated by electrophoresis on 4-12% Tris-glycine gels (for analysis of full-length hPMS2) or 4-20% Tris-glycine gels (for analysis of hPMS2-134). Gels were electroblotted onto Immobilon-P (Millipore) in 48 mM Tris base, 40 mM glycine, 0.0375% SDS, 20% methanol and blocked overnight at 4° C. in Tris-buffered saline plus 0.05% Tween-20 and 5% condensed milk. Filters were probed with a polyclonal antibody generated against residues 2-20 of hPMS2 (Santa Cruz Biotechnology, Inc.) and a horseradish peroxidase conjugated goat anti-rabbit secondary antibody, using chemilluminescence for detection (Pierce).

Linear DNA fragments containing hPMS2 and hMLH1 cDNA sequences were prepared by PCR, incorporating sequences for in vitro transcription and translation in the sense primer. A full-length hMLH1 fragment was prepared using the sense primer 5'-ggatcctaatacgactcactatagg-gagaccaccatgtcgttcgtggcaggg-3' (codons 1-6) (SEQ ID NO: 3) and the antisense primer 5'-taagtcttaagtgctaccaac-3' (located in the 3' untranslated region, nt 2411-2433) (SEQ ID NO: 4), using a wild-type hMLH1 cDNA clone as template. A full-length hPMS2 fragment was prepared with a sense primer comprising 5'-atggagcgagctgagagc-3' (codons 1-6; SEQ ID NO: 5) and the antisense primer 5'-aggttagtgaa-gactctgtc-3' (located in 3' untranslated region, nt 2670-2690) (SEQ ID NO: 6) using a cloned hPMS2 cDNA as template. A fragment encoding the amino-terminal 134 amino acids of hPMS2 was prepared using the same sense primer and the antisense primer 5'-agtcgagttccaaccttcg-3 (SEQ ID NO: 7). A fragment containing codons 135-862 of hPMS135 was generated using the sense primer 5'-ggatcctaatacgactcactatagg-gagaccaccatgatgtttgatcacaatgg-3' (codons 135-141) (SEQ ID NO:8) and the same antisense primer as that used for the full-length hPMS2 protein. These fragments were used to produce proteins via the coupled transcription-translation system (Promega). The reactions were supplemented with $^{35}$S-labelled methionine or unlabelled methionine, as indicated in the text. The PMS135 and hMLH1 proteins could not be simultaneously radiolabelled and immunoprecipitated because of their similar molecular weights precluded resolution. Lower molecular weight bands are presumed to be degradation products and/or polypeptides translated from alternative internal methionines.

Immunoprecipitation. Immunoprecipitations were performed on in vitro translated proteins by mixing the translation reactions with 1 μg of the MLH1 specific monoclonal antibody (mAB) MLH14 (Oncogene Science, Inc.), a polyclonal antibody generated to codons 2-20 of hPMS2 described above, or a polyclonal antibody generated to codons 843-862 of hPMS2 (Santa Cruz Biotechnology, Inc.) in 400 μl of EBC buffer (50 mM Tris, pH 7.5, 0.1 M NaCl, 0.5% NP40). After incubation for 1 hr at 4° C., protein A sepharose (Sigma) was added to a final concentration of 10% and reactions were incubated at 4° C. for 1 hour. Proteins bound to protein A were washed five times in EBC and separated by electrophoresis on 4-20% Tris-glycine gels, which were then dried and autoradiographed.

Biochemical assays for mismatch repair. MMR activity in nuclear extracts was performed as described, using 24 fmol of substrate (12,25). Complementation assays were done by adding ~100 ng of purified MutLα or MutSα components to 100 μg of nuclear extract, adjusting the final KCl concentration to 100 mM (4, 10, 30). The substrates used in these experiments contain a strand break 181 nucleotides 5' or 125 nucleotides 3' to the mismatch. Values represent experiments performed at least in duplicate.

EXAMPLE 3

Carboxy Terminus of hPMS2 Mediates Interaction Between hPMS2 and hMLH1

To elucidate the mechanism by which hPMS2-134 affected MMR, we analyzed the interaction between hPMS2 and hMLH1. Previous studies have shown that these two proteins dimerize to form a functionally active complex (12, 28). Proteins were synthesized in vitro using reticulocyte lysates, employing RNA generated from cloned templates. The full-length hMLH1 and hPMS2 proteins bound to each other and were co-precipitated with antibodies to either protein, as expected (data not shown). To determine the domain of hPMS2 which bound to hMLH1, the amino terminus (codons 1-134), containing the most highly conserved domain among mutL proteins (19,24), and the carboxyl terminus (codons 135-862) were separately cloned and proteins produced in vitro in coupled transcription-translation reactions. When a $^{35}$S-labelled, full length hMLH1 protein (FIG. 5A, lane 5) was mixed with the unlabelled carboxyl terminal hPMS2 polypeptide, a monoclonal antibody (mAb) to the carboxyl terminus of hPMS2 efficiently immunoprecipitated the labeled hMLH1 protein (lane 1). No hMLH1 protein was precipitated in the absence of hPMS2 (lane 2). Conversely, when the $^{35}$S-labelled carboxyl-terminus of hPMS2 (lane 3) was incubated with unlabelled, full-length hMLH1 protein, an anti-hMLH1 mAb precipitated the hPMS2 polypeptide (lane 4). In the absence of the unlabelled hMLH1 protein, no hPMS2 protein was precipitated by this mAb (lane 6). The same antibody failed to immunoprecipitate the amino-terminus of hPMS2 (amino acids 1-134) when mixed with unlabelled MLH1 protein (FIG. 5B, lane 1). This finding was corroborated by the converse experiment in which radiolabelled hPMS2-134 (FIG. 5C, lane 1) was unable to coprecipitate radiolabelled MLH1 when precipitations were done using an N-terminal hPMS2 antibody (FIG. 5C, lane 2) while this antibody was shown to be able to coprecipitate MLH1 when mixed with wild-type hPMS2 (FIG. 5C, lane 4).

The initial steps of MMR are dependent on two protein complexes, called MutSα and MutLα (14). As the amino terminus of hPMS2 did not mediate binding of hPMS2 to hMLH1, it was of interest to determine whether it might instead mediate the interaction between the MutL□ complex (composed of hMLH1 and hPMS2, ref. 12) and the MutSα complex (composed of MSH2 and GTBP, ref. 4). Because previous studies have demonstrated that MSH2 and the MutLα components do not associate in solution (28), we were unable to assay for direct hPMS2-134:MutSα interaction. We therefore used a different approach to address this issue, and attempted to complement nuclear extracts from the various SH cell lines with MutSα or MutLα. If the truncated protein present in the PMS2-134 expressing SH cells was binding to MutSα and lowering its effective concentration in the extract, then adding intact MutSα should rescue the MMR defect in such extracts. Purified MutSα added to such extracts had no effect (FIG. 6). In contrast, addition of intact MutLα to the extract completely restored directional repair to the extracts from PMS2-134 cells (FIG. 6).

The results described above lead to several conclusions. First, expression of the amino-terminus of hPMS2 results in an increase in microsatellite instability, consistent with a replication error (RER) phenotype. That this elevated microsatellite instability is due to MMR deficiency was proven by evaluation of extracts from stably transduced cells. Interestingly, the expression of PMS2-134 resulted in a polar defect in MMR, which was only observed using heteroduplexes designed to test repair from the 5' direction (no significant defect in repair from the 3' direction was observed in the same extracts). Interestingly, cells deficient in hMLH1 also have a polar defect in MMR, but in this case preferentially affecting repair from the 3' direction (5). It is known from previous studies in both prokaryotes and eukaryotes that the separate enzymatic components mediate repair from the two different directions. Our results, in combination with those of Drummond et al., strongly suggest a model in which 5' repair is primarily dependent on hPMS2 while 3' repair is primarily dependent on HMLH1. It is easy to envision how the dimeric complex between PMS2 and MLH1 might set up this directionality. The combined results also demonstrate that a defect in directional MMR is sufficient to produce a RER+ phenotype.

We anticipated that the dominant negative function of the PMS2-134 polypeptide resulted from its binding to MLH1 and consequent inhibition of MutLα function. This hypothesis was based in part on the fact that the most highly conserved domain of the PMS2 gene is located in its amino terminus, and the only known biochemical partner for PMS2 is MLH1. Our binding studies revealed, however, that the carboxyl terminus of PMS2, rather than the highly conserved amino terminus, actually mediated binding to MLH1. This result is consistent with those recently obtained in *S. cerevisciae*, in which the MLH1-interacting domain of PMS1 (the yeast homolog of human PMS2) was localized to its carboxyl-terminus (23). Our add-back experiments additionally showed that the hPMS2-134 mutant was not likely to mediate an interaction with the MutSα complex (FIG. 6). The best explanation at present to explain the various observations made here is that the hPMS2-134 polypeptide does not inhibit the initial steps in MMR, but rather interacts with and inhibits a downstream component of the pathway, perhaps a nuclease required for repair from the 5' direction.

The demonstration that the hPMS2-134 mutation can confer a dominant negative MMR defect to transfected cells helps to explain the phenotype of the kindred in which this mutant was discovered. Three individuals from this kindred were found to carry the mutation, a father and his two children. Both children exhibited microsatellite instability in their normal tissues and both developed tumors at an early age, while the father had no evidence of microsatellite instability in his normal cells and was completely healthy at age 35. The only difference known to us with respect to the MMR genes in this family is that the father's mutant allele was expressed at lower levels than the wild-type allele as assessed by sequencing of reverse transcriptase-PCR products of RNA from lymphocytes. The children expressed both alleles at approximately equal levels (Parsons et al. and unpublished observations). We suspect that the dominant negative attribute of the hPMS2-134 mutant will only be manifest when it is present at sufficient concentrations (at least equimolar), thus explaining the absence of MMR deficiency in the father. The reason for the differential expression of the hPMS2-134 allele in this kindred is not clear, though imprinting is a possibility. Hopefully, the ascertainment of additional, larger kindreds with such mutations will facilitate the investigation of this issue.

REFERENCES

1. Baker S. M., Bronner, C. E., Zhang, L., Plug, A. W., Robatez, M., Warren, G., Elliott, E. A., Yu, J., Ashley, T., Arnheim, N., Bradley, N., Flavell, R. A., and Liskay, R. M. 1995. Male defective in the DNA mismatch repair gene PMS2 exhibit abnormal chromosome synapsis in meiosis. Cell 82:309-319.

2. Bronner, C. E., Baker, S. M., Morrison, P. T., Warren, G., Smith, L. G., Lescoe, M. K., Kane, M., Earabino, C., Lipford, J., Lindblom, A., Tannergard, P., Bollag, R. J., Godwin, A., R., Ward, D. C., Nordenskjold, M., Fishel, R., Kolodner, R., and Liskay, R. M. 1994. Mutation in the DNA mismatch repair gene homologue hMLH1 is associated with hereditary non-polyposis colon cancer. Nature 368:258-261.
3. de Wind N., Dekker, M., Bems, A., Radman, M., and Riele, H. T. 1995. Inactivation of the mouse Msh2 gene results in mismatch repair deficiency, methylation tolerance, hyperrecombination, and predisposition to cancer. Cell 82:321-300.
4. Drummond, J. T., Li, G. M., Longley, M. J., and Modrich, P. 1995. Isolation of in hMSH2-p160 heterodimer that restores mismatch repair to tumor cells. Science 268:1909-1912.
5. Drummond, J. T., Anthoney, A., Brown, R., and Modrich, P. 1996. Cisplatin and adriamycin resistance are associated with MutLα and mismatch repair deficiency in an ovarian tumor cell line. J. Biol. Chem. 271:9645-19648.
6. Edelmann, W., Cohen, P. E., Kane, M., Lau, K., Morrow, B., Bennett, S., Umar, A., Kunkel, T., Cattoretti, G., Chagnatti, R., Pollard, J. W., Kolodner, R. D., and Kucherlapati, R. 1996. Meiotic pachytene arrest in MLH1-deficient mice. Cell 85:1125-1134.
7. Fishel, R., Lescoe, M., Rao, M. R. S., Copeland, N. J., Jenkins, N. A., Garber, J., Kane, M., and Kolodner, R. 1993. The human mutator gene homolog MSH2 and its association with hereditary nonpolyposis colon cancer. Cell 7:1027-1038.
8. Green, S., Issemann, I., and Sheer, E. 1988. A versatile in vivo eucaryotic expression vector for protein engineering. Nuc. Acid Res. 16:369.
9. Hamilton, S. R., Liu, B., Parsons, R., E., Papadopoulos, N., Jen, J., Powell, S. M., Krush, A. J., Berk, T., Cohen, Z., tetu, B., Kinzler, K. W., and Vogelstein, B. 1995. The molecular basis of Turcot's syndrome. N. Eng. J. Med. 332:839-847.
10. Holmes, J., Clark, S., and Modrich, P. Strand specific mismatch correction in nuclear extracts of human and *Drosophila melanogaster* cell lines. (1990). Proc. Natl. Acad. Sci. USA 87:5837-5841.
11. Leach, F. S., Nicolaides, N. C, Papadopoulos, N., Liu, B., Jen, J., Parsons, R., Peltomaki, P., Sistonen, P., Aaltonen, L. A., Nystrom-Lahti, M., Guan, X. Y., Zhang, J., Meltzer, P. S., Yu, J. W., Kao, F. T., Chen, D. J., Cerosaletti, K. M., Fournier, R. E. K., Todd, S., Lewis, T., Leach R. J., Naylor, S. L., Weissenbach, J., Mecklin, J. P., Jarvinen, J. A., Petersen, G. M., Hamilton, S. R., Green, J., Jass, J., Watson, P., Lynch, H. T., Trent, J. M., de la Chapelle, A., Kinzler, K. W., and Vogelstein, B. 1993. Mutations of a mutS homolog in hereditary non-polyposis colorectal cancer. Cell 75:1215-1225.
12. Li, G.-M., and Modrich, P. 1995. Restoration of mismatch repair to nuclear extracts of H6 colorectal tumor cells by a heterodimer of human mutL homologs. Proc. Natl. Acad. Sci. USA 92:1950-1954.
13. Liu, B., Parsons, R., Papadopoulos, N., Nicolaides, N. C., Lynch, H. T., Watson, P., Jass, J. R., Dunlop, M., Wyllie, A., Peltomaki, P., de la Chapelle, A., Hamilton, S. R., Vogelstein, B., and Kinzler, K. W. 1996. Analysis of mismatch repair genes in hereditary non-polyposis colorectal cancer patients. Nat. Med. 2:169-174.
14. Modrich, P. 1994. Mismatch repair, genetic stability, and cancer. Science 266: 1959-1960.
15. Nicolaides, N. C., Gualdi, R., Casadevall, C., Manzella, L., and Calabretta, B. 1991. Positive autoregulation of c-myb expression via MYB binding in the 5' flanking region of the human c-myb gene. Mol. Cell. Biol. 11:6166-6176.
16. Nicolaides, N. C., Correa, I., Casadevall, C., Travali, S., Soprano, K. J., and Calabretta, B. 1992. The Jun family members, c-JUN and JUND, transactivate the human c-myb promoter via an Ap1 like element. J. Biol. Chem. 267, 19665-19672.
17. Nicolaides, N. C., Papadopoulos, N., Liu, B., Wei, Y. F., Carter, K. C., Ruben, S. M., Rosen, C. A., Haseltine, W. A., Fleischmann, R. D., Fraser, C. M., Adams, M. D., Venter, C. J., Dunlop, M. G., Hamilton, S. R., Petersen, G. M., de la Chapelle, A., Vogelstein, B., and kinzler, K. W. 1994. Mutations of two PMS homologs in hereditary nonpolyposis colon cancer. Nature 371: 75-80.
18. Nicolaides N. C., Kinzler, K. W., and Vogelstein, B. 1995. Analysis of the 5' region of PMS2 reveals heterogenous transcripts and a novel overlapping gene. Genomics 29:329-334.
19. Nicolaides, N. C., Carter, K. C., Shell, B. K., Papadopoulos, N., Vogelstein, B., and Kinzler, K. W. 1995. Genomic organization of the human PMS2 gene family. Genomics 30:195-206.
20. Nicolaides, N. C., Palombo, F., Kinzler, K. W., Vogelstein, B., and Jiricny, J. 1996. Molecular cloning of the N-terminus of GTBP. Genomics 31:395-397.
21. Palombo, F., Hughes, M., Jiricny, J., Truong, O., Hsuan, J. 1994. Mismatch repair and cancer. Nature 36:417.
22. Palombo, F., Gallinari, P., Iaccarino, I., Lettieri, T., Hughes, M. A., Truong, O., Hsuan, J. J., and Jiricny, J. 1995. GTBP, a 160-kilodalton protein essential for mismatch-binding activity in human cells. Science 268:1912-1914.
23. Pang, Q., Prolla, T. A., and Liskay, R. M. 1997. Functional domains of the *Saccharomyces cerevisiae* Mlh1p and Pms1p DNA mismatch repair proteins and their relevance to human hereditary nonpolyposis colorectal cancer-associated mutations. Mol. Cell. Biol. 17:4465-4473.
24. Papadopoulos, N., Nicolaides, N. C., Wei, Y. F., Carter, K. C., Ruben, S. M., Rosen, C. A., Haseltine, W. A., Fleischmann, R. D., Fraser, C. M., Adams, M. D., Venter, C. J., Dunlop, M. G., Hamilton, S. R., Petersen, G. M., de la Chapelle, A., Vogelstein, B., and kinzler, K. W. 1994. Mutation of a mutL homolog is associated with hereditary colon cancer. Science 263:1625-1629.
25. Parsons, R., Li, G. M., Longley, M. J., Fang, W. H., Papadopolous, N., Jen, J., de la Chapelle, A., Kinzler, K. W., Vogelstein, B., and Modrich, P. 1993. Hypermutability and mismatch repair deficiency in RER+ tumor cells. Cell 75:1227-1236.
26. Parsons, R., Li, G. M., Longley, M., Modrich, P., Liu, B., Berk, T., Hamilton, S. R., Kinzler, K. W., and Vogelstein, B. 1995. Mismatch repair deficiency in phenotypically normal human cells. Science 268:738-740.
27. Perucho, M. 1996. Cancer of the microsatellite mutator phenotype. Biol Chem. 377:675-684.
28. Prolla, T. A, Pang, Q., Alani, E., Kolodner, R. A., and Liskay, R. M. 1994. MLH1, PMS1, and MSH2 Interaction during the initiation of DNA mismatch repair in yeast. Science 264:1091-1093.
29. Strand, M., Prolla, T. A., Liskay, R. M., and Petes, T. D. Destabilization of tracts of simple repetitive DNA in yeast by mutations affecting DNA mismatch repair. 1993. Nature 365:274-276.
30. Su, S. S., Lahue, R. S., Au, K. G., and Modrich, P. 1988. Mispair specificity of methyl directed DNA mismatch corrections in vitro. J. Biol. Chem. 263:6829-6835.

We claim:

1. A method for generating a library of mutant mammalian cells comprising:

expressing in mammalian cells a polynucleotide encoding a dominant-negative mismatch repair protein wherein the protein comprises the N-terminal 133 amino acids of human PMS2, said polynucleotide operably linked to a promoter, wherein expression of said polypeptide inhibits mismatch repair of said mammalian cells, thereby producing a library of mutant mammalian cells.

2. A method for generating a library of mutant mammalian cells comprising:

expressing in mammalian cells a polynucleotide encoding human PMS2-134, said polynucleotide operably linked to a promoter, wherein expression of said polypeptide inhibits mismatch repair of said mammalian cells, thereby producing a library of mutant mammalian cells.

* * * * *